United States Patent [19]
Asculai

[11] 3,955,923
[45] May 11, 1976

[54] SEROLOGIC REACTION METHOD
[75] Inventor: Samuel Simon Asculai, Hampton, N.J.
[73] Assignee: Ortho Pharmaceutical Corporation, Raritan, N.J.
[22] Filed: Jan. 13, 1973
[21] Appl. No.: 328,219

[52] U.S. Cl. .............................. 23/230 B; 424/12
[51] Int. Cl.² ........................................ G01N 33/16
[58] Field of Search ............... 23/230 B; 424/12; 350/95

[56] References Cited
UNITED STATES PATENTS

| | | | |
|---|---|---|---|
| 2,041,290 | 5/1936 | Jackson | 350/95 X |
| 3,088,875 | 5/1963 | Fisk | 424/12 X |
| 3,415,361 | 12/1968 | Adams, Jr. et al. | 23/230 B UX |
| 3,617,222 | 11/1971 | Matte | 23/230 B X |

OTHER PUBLICATIONS

Naik et al.; "An Immunological Pregnancy Test"; The Indian Journal of Medical Sciences, 1963; pp. 506–509.

"Gradwohl's Clinical Laboratory Methods & Diagnosis 7th Ed.", C. V. Mosby Co., St. Louis, 1970, pp. 1471–1475, 1579–1582.

Davidson et al., "Todd–Sanford Clinical Diagnosis by Laboratory Methods", 14th Ed. W. B. Saunders Co., Phil., Pa., 1969, pp. 1185–1186.

Gradwohl's, "Clinical Laboratory Methods & Diagnosis", 7th Ed., C. V. Mosby Co., Saint Louis, 1970, Vol. 2, pp. 1518–1522.

Primary Examiner—Morris O. Wolk
Assistant Examiner—Arnold Turk
Attorney, Agent, or Firm—Benjamin F. Lambert

[57] ABSTRACT

A method for detecting the end point in immunochemical and serodiagnostic tests involving agglutination is described wherein the test is carried out on a curved slide having a curvature sufficient to produce a discernible pattern at the end point.

13 Claims, No Drawings

SEROLOGIC REACTION METHOD

The present invention is concerned with immunochemical and serodiagnostic tests and, in particular, with an improved method for determining the end point in such tests where the end point determination depends upon the presence or absence of agglutination.

Agglutination is a reaction in which cells, such as bacteria or blood corpuscles, suspended in a liquid collect into clumps or floccules. The reaction occurs when the cell suspension is treated with serum which has been immunized against cells of the same kind and species, especially as a serologic response to a specific antibody.

The immunochemical reactions which are the subject of this invention are most commonly laboratory tests which have as their objective the determination of the presence or absence of antigens or antibodies in body fluids such as serum and urine, for example, as an aid in the diagnosis of certain physiological or pathological conditions in humans and animals. The immunochemical reaction may result in the formation of a precipitate, in which case it is known as a precipitin reaction. Where the reaction is between substances distributed in a liquid medium, and at least one of the substances is a solid which becomes agglomerated, the reaction is known as an agglutination reaction. The particular effect obtained will depend upon the combination of reagents and test liquid employed. The formation of precipitates or the agglutination or inhibition of agglutination of specially treated particles is sometimes readily seen in the way the precipitates form, or the particles arrange themselves following the reaction. Tests for blood group type, pregnancy, mononucleosis and similar phenomena are just a few of the immunochemical tests which may be carried out in this manner. The difficulty encountered with most of these tests, however, is that it usually requires a trained eye to determine unequivocally whether the test result is positive or negative, i.e. whether agglutination or inhibition of agglutination has taken place. An untrained person such as a housewife, for example, would undoubtedly have great difficulty making such a determination in a pregnancy test, for example, using currently available test methods.

In recent times, several techniques have been developed in which the antigen is first adsorbed onto a carrier such as various erythrocytes, bentonite and polystyrene latex particles, to mention a few. This procedure facilitates the visualization of the reaction by providing a more easily read end point. However, in spite of the newly developed techniques, difficulty is still encountered by the layman in making an unambiguous determination as to whether the test is positive or negative. The degree of difficulty encountered generally depends upon the sensitivity of the particular test employed.

It is known in the art that certain immunochemical tests, such as pregnancy tests, for example, can be carried out on slides wherein the reaction is between substances suspended in a liquid. It is also known in the art to use slides which contain all the necessary reagents for performing immunochemical or diagnostic tests in solid, dry, stable spot deposits which, upon being moistened, are reconstituted to the respective test reagents with the liquid to be tested. Due to the sensitivity of the test, in most cases, it is often difficult in these prior art methods to determine when the end point has been reached, i.e., whether agglutination or inhibition of agglutination has occurred. Frequently, it is necessary to use additional equipment such as a light source over the slide or a magnifying glass to simplify the test reading.

Thus, there is still a need for a simplified immunochemical test procedure which renders the result immediately observable by the person making the test without equivocation.

GENERAL DESCRIPTION OF THE INVENTION

A principal object of the present invention is to provide an immunochemical test method for the determination of antigens in body fluids.

Another object of the invention is to provide an immunochemical test method which does not require elaborate equipment but still allows the person performing the test to determine accurately whether agglutination or inhibition of agglutionation has occurred within a few minutes after the test has been completed. These and other objects and advantages of the present invention will become apparent from the following description.

In accordance with the present invention, when the immunochemical test is carried out in a curved, concave slide agglutination is indicated by the formation of a distinct pattern which is clearly visible even to the untrained eye. If no agglutination takes place, no patterns forms. The formation of a distinct pattern is best illustrated by the pregnancy test where a mosaic like pattern develops at the end point. When, as in the prior art, a flat slide is employed in the test, no distinct pattern is formed when agglutination takes place and, depending upon the sensitivity of the test, the concentration of the test reagents, etc., it is often difficult to distinguish between a positive and a negative test.

DESCRIPTION OF THE PREFERRED EMBODIMENTS

The method of the present invention depends upon inhibition of the reaction between an anti-serum, such as human chorionic gonadotrophin (HCG) anti-serum, which has been diluted in buffers, and a particulate antigen by the hormone present in the patient's body fluid, such as urine, for example. The principal advantage gained by employing a curved slide in the test is that the discrimination between a positive test (no pattern) and a negative test (distinct pattern) can be made without equivocation even by an untrained eye. Thus it is now possible for a layman, by employing the present invention, to carry out immunochemical and serodiagnostic tests with certainty as to the result.

The surface of the test slide must be curved if a distinct pattern is to be obtained. Any slide having a concave curved surface may be employed. The slide may be a portion of a sphere such as a watch glass, for example, or it may be any curved surface. The only essential requirement is that the curvature of the slide should be sufficient to produce a discernible pattern at the end point. It is preferred, however, to use a concave portion of a sphere as the test surface. Both glass and plastic materials may be employed. Where a plastic material is employed, the surface of the plastic should be wettable. Suitable plastic materials for this purpose are general purpose styrene and acrylic resins. Other materials, such as waxed paper or other specially treated paper products, for example, may also be employed as the test surface.

Slides having varying dimensions and concavities may be employed. The dimension of the particular slide employed will depend upon the particular test to be made and the amount of material to be employed. It is convenient, however, to use a watch glass having a diameter between about 40 mm and 65 mm and a concavity ranging from about 3.08 mm to about 7.30 mm. The particular dimensions of the slide employed are not critical. The slide need only have a curvature sufficient to produce a discernible pattern (agglutination) or indicate the lack of a pattern (inhibition of agglutination).

It is not known exactly why a distinct pattern forms when the test is carried out on a curved surface. One theory is that the agglutinated particles, once formed, tend to roll down the wall of the curved surface and concentrate in certain areas with other agglutinates resulting in a larger mosaic of agglutinates.

The immunochemical test method will be principally illustrated with respect to reagents for an immunochemical or diagnostic test for detecting the presence of human chorionic gonadotrophin (HCG) in urine. The test is utilized in the diagnosis of pregnancy. However, it will be understood by those skilled in the art that the principles of the invention are not to be regarded as being limited thereto, but may be extended to a wide range of immunochemical reactions and test reagents.

The pregnancy test is an inhibition test and depends on the presence of human chorionic gonadotrophin (HCG) in the urine of the patient. The level of HCG is generally sufficiently high for detection about 13 days after the first period is missed. In one aspect of the invention, the urine specimen is placed on the slide and to it is added a quantity of pregnancy anti-serum. Generally, a drop of each liquid is sufficient. The slide may be placed on a dark background for better detection of the end point. Alternatively, a dye may be employed for this purpose. Dyes such as mint green shade dye or erythrosine are suitable. When a dye is employed it is usually added to the anti-serum. Generally, concentrations of dye from about 0.030 mg/ml to 0.100 mg/ml are employed. The antigen suspension, consisting of latex particles coated with HCG, is added to the urine-antiserum mixture and the slide is then rocked for about 30 – 60 seconds. Best results are obtained when a rocking, rotating motion is employed. Rocking for longer periods tends to result in a weaker pattern. The slide and contents, after rocking are held static for several minutes. The optimum time for best results is 6 – 10 minutes. If the urine contains no HCG, i.e. the patient is not pregnant, a unique, mosaic like pattern develops within several minutes. The pattern is generally still visible even after 10 minutes have elapsed. If the test urine contains 3.5 I.U. of HCG or more per ml. of urine, no pattern develops between 0–10 minutes, i.e. the patient is pregnant.

An alternate test for pregnancy is a direct test which depends on the presence of human chorionic gonadotrophin (HCG) in the urine of the patient. In the direct test an anti-serum complex is added directly to the urine specimen. The level of HCG is generally sufficiently high for detection by this procedure about 36 days after the onset of the last menstrual period. The urine specimen is placed on the slide and to it is added a quantity of buffer solution. Generally, a drop of each liquid is sufficient. The anti-serum complex, consisting of latex particles coated with antibodies to HCG, is added to the urine-buffer mixture and the slide is then rocked for about 15 – 30 seconds. The slide and contents, after rocking, are held static for several minutes. The optimum time for best results is 3 – 6 minutes. If the urine contains 1.0 I.U. of HCG or more per ml. of urine, i.e. patient is pregnant, agglutination takes place. When the direct test is carried out on a concave, curved test surface, a distinct easily discernible mosaic like pattern develops within several minutes after the rocking is stopped, where agglutination takes place. The pattern is generally still visible even after ten minutes have elapsed. If the test urine contains no HCG, no pattern develops between 0 – 10 minutes, i.e., the patient is not pregnant. Thus, when the direct test method is employed, the appearance of agglutination is an indication of pregnancy while the absence of agglutination is an indication that the patient is not pregnant.

As indicated above, the presence or absence of HCG in the urine is detected by agglutination or the inhibition of agglutination of the carrier particles. Similar agglutination or inhibition of agglutination, is to be observed in the case of other types of immunochemical reagents and test liquids.

The immunochemical reactions can also be carried out on a reconstituted mixture of the anti-serum. When such is the case, the anti-serum, with or without a dye, is air-dried on the curved test surface. The dry anti-serum is reconstituted with one drop of the body fluid to be tested and the antigen suspension is added thereto. A unique pattern will form within minutes if agglutination takes place.

The following examples are given as specific illustrations. It is to be understood, however, that the invention is not to be limited to the specific details of the examples.

EXAMPLE I a. Preparation of pregnancy anti-serum

A relatively concentrated solution of human chorionic gonadotrophin is prepared by dissolving human chorionic gonadotrophin, assaying between about 1700 and 2200 international units per milligram, in 0.15 N saline to give a concentration of 100,000 international units per milliliter. This solution is mixed with an equal volume of Freund's complete adjuvant. The human chorionic gonadotrophin was supplied by the Vitamerican Company.

A second and more dilute solution of human chorionic gonadotrophin was prepared by dissolving human chorionic gonadotrophin in 0.15 N saline to give a concentration of 10,000 international units per milliliter. Again the human chorionic gonadotrophin employed was supplied by Vitamerican Company and assayed between about 1700 and about 2200 international units per milligram.

Rabbits are employed as the host animal. One milliliter of the concentrated solution containing 50,000 international units of human chorionic gonadotrophin per milliliter is given intramuscularly to each rabbit, followed three weeks later by one intravenous injection of the dilute solution containing 10,000 international units of human chorionic gonadotrophin on each of three consecutive days. All of the rabbits are bled by cardiac puncture 10 to 14 days after the last injection and the serum from each rabbit is collected separately. Each rabbit serum, after heating at 56°C. for 30 minutes, is tested against solutions of human chorionic gonadotrophin containing 250 and 100 international units per milliliter of the antigen, respectively. The anti-sera showing precipitation (++) with the 100 international units per milliliter sample are pooled together. To the rabbit anti-sera pooled together is added sodiumethylmercurithiosalicylate merthiolate to give a final concentration of 1:5000. One volume of the pooled anti-sera is diluted with 15 volumes of the following solution: 0.4365 g. boric acid, 0.1 g. NaCl, 0.234 ml. 5 N NaOH, 6 g. sucrose, 1.0 g. bovine serum albumin, sodium citrate dihydrate 4.0 g.; distilled water q.s. to 100 ml.; the pH is adjusted to 8.2 with NaOH or HCl. The diluted anti-serum is sterile filtered through a D-8 to a D-10 asbestos pad.

b. Preparation of antigen suspension

One volume of a polystyrene latex obtained from Difco Laboratories of Detroit, Michigan, identified as Bacto-Latex 0.81 and having an average particle diameter of 0.81 micron is diluted with 9 volumes of a borate buffer having a pH of 8.2. The borate buffer is prepared by adding 35 milliliters of 0.05 molar sodium borate to 65 milliliters of 0.2 molar boric acid and adding 0.85 gram of sodium chloride. The concentration of polystyrene solids in the Bacto-Latex is 2% by volume and the concentration of polystyrene solids in the diluted borate buffer solution is about 0.2% by volume. One volume of the diluted latex (1% polystyrene solids) is further diluted with an equal volume of the borate buffer solution containing 40 international units per milligram of human chorionic gonadotrophin. After thorough mixing, the mixture is left overnight at 2° – 8°C. before using.

c. Test procedure

A drop of urine specimen containing no HCG is placed on a standard 40 mm glass concave slide having an arc radius of 3.6 cm. One drop of anti-serum containing antibodies to HCG is added and the mixture is mixed well with an applicator stick. Two drops of antigen, consisting of latex particles coated with HCG, are added to the urine-antiserum mixture and the entire mixture is mixed well with an applicator stick. After mixing, the slide is rocked with a rotating motion for 30 seconds and then held static for ten minutes. A unique easily discernible pattern develops after 3 – 4 minutes which indicates that no HCG is present in the urine. The pattern is still visible after 10 minutes have elapsed.

EXAMPLE II

To a drop of the anti-serum prepared in Example I above is added 0.36 mg/ml of mint green shade dye and the mixture is air-dried on a standard 40 mm glass concave slide having an arc radius of 3.6 cm. The dry serum is reconstituted with one drop of urine containing at least five international units (I.U.) of human chorionic gonadotrophin per milliliter. To the reconstituted mixture are added two drops of polystyrene latex coated with HCG. After mixing, the slide is rocked with a rotating motion for 30 seconds. The slide and contents are then allowed to come to rest and are held static for ten minutes. No pattern develops after 3–4 minutes. No pattern is visible even after ten minutes.

EXAMPLE III

Test for Infectious Mononucleosis

A known test for the detection of infectious mononucleosis antibodies is carried out as follows:

One drop of thoroughly mixed MONOSPOT* reagent I is placed in a 40 mm glass concave slide having an arc radius of 3.6 cm and the slide is marked A. One drop of MONOSPOT* reagent II is placed in a 40 mm glass concave slide having an arc radius of 3.6 cm and the slide is marked B. One drop of the serum is added to each of the two glass slides, and reagents and sera are mixed with an applicator stick. Ten microliters of suspended MONOSPOT* indicator red blood cells are blended into the mixture in each slide. The slides and contents are rocked about 25 times with a rotating motion in 30 seconds. The results are observed immediately by placing the watch glasses on a white background.

*Trademark of Ortho Pharmaceutical Corp., Raritan, N.J.

If the agglutination in slide A is stronger than that in slide B, the serum under test is positive for infectious mononucleosis. If the agglutination in watch glass A is the same as or weaker than that in B, the serum under test is negative for infectious mononucleosis.

EXAMPLE IV

Rh Typing

Two drops of a 40–50% suspension of human red blood cells are added to a 40 mm glass concave slide having an arc radius of 3.6 cm (whole human blood may also be used). One drop of Anti-$Rh_o$ (Anti-D) Typing Serum (a product of ORTHO Diagnostics, a division of ORTHO PHARMACEUTICAL CORPORATION) is blended into the red cell suspension with an applicator stick. The slide and contents are rocked 50 times in one minute with a rotating motion. The results are observed immediately by placing the slide on a white background.

The presence of agglutination in the slide is indicative of Rh-positive cells. The absence of agglutination is indicative of Rh-negative cells.

EXAMPLE V

Blood Grouping

One drop of Anti-A Serum (a product of ORTHO Diagnostics, a division of ORTHO PHARMACEUTICAL CORPORATION) is placed in a 40 mm glass concave slide having an arc radius of 3.6 cm and marked 1. One drop of Anti-B Serum (a product of ORTHO Diagnostics, a division of ORTHO PHARMACEUTICAL CORPORATION) is placed in a 40 mm glass concave slide having an arc radius of 3.6 cm and marked 2. Two drops of a 10% suspension of human red blood cells are added to each of the two slides (whole blood may also be used). The antisera and blood cells are blended with an applicator stick and each slide is rocked about 25 times in 30 seconds with a rotating motion. The results are observed immediately by placing the slides on a white background.

The results of the test are interpreted by referring to the following table:

| SLIDE 1 | SLIDE 2 | BLOOD GROUP |
|---|---|---|
| No Agglutination | No Agglutination | O |
| Agglutination | No Agglutination | A |
| No Agglutination | Agglutination | B |
| Agglutination | Agglutination | AB |

Reverse or Serum Grouping is done in an identical fashion except that AFFIRMAGEN* Reagent Red Cells are used in place of the test red blood cells and the Anti-A and Anti-B sera are replaced by the human serum to be tested.

*Trademark of Ortho Pharmaceutical Corp., Raritan, N.J.

EXAMPLE VI

Direct Test for Pregnancy

One drop of a urine specimen containing at least 1.0 I.U. HCG per ml. is placed on a standard 65 mm glass concave slide. One drop of the direct test buffer is added to the urine and the mixture is mixed with an applicator stick. One drop of antiserum complex, consisting of latex particles coated with antibodies to HCG, is added to the urine-buffer mixture and the entire mixture is mixed well with an applicator stick. After mixing, the slide is rocked with a rotating motion for 15 seconds and is then held static for 10 minutes. A unique easily discernible pattern develops after 3 – 4 minutes and the pattern is still visible after ten minutes have elapsed.

While the invention has been described with reference to the specific embodiments, it is to be understood that it is not to be limited thereto, but it is to be construed broadly and restricted solely by the scope of the appended claims.

What is claimed is:

1. In an immunochemical or serodiagnostic test reaction, wherein the end point is determined by the presence or absence of agglutination, which comprises reacting the body fluid to be tested with an anti-serum on a test surface and adding an antigen complex to the mixture of body fluid and anti-serum, said antigen complex consisting of solid particles coated with the antigen, the improvement which comprises performing the test on a test surface having a concave curvature sufficient to produce a discernible pattern at the end point where agglutination occurs, the absence of said pattern being an indication of the inhibition of agglutination by the soluble antigens present in the body fluid, said test surface being a portion of a sphere having a depth from about 3.08 mm. to about 7.30 mm. and a diameter between about 40 mm. and 65 mm.

2. The method of claim 1 wherein the curved test surface is a glass surface.

3. The method of claim 1 wherein the curved test surface is a plastic surface.

4. The method of claim 1 wherein the solid particles are selected from erythrocytes, bentonite and polystyrene.

5. The method of claim 1 wherein the anti-serum additionally contains a dye.

6. The method of claim 5 wherein the dye is selected from mint-green dye and erythrosine dye.

7. In an immunochemical test for the diagnosis of pregnancy, wherein the end point is determined by the presence or absence of agglutination, which comprises reacting a urine specimen with an anti-serum containing antibodies to human chorionic gonadotrophin on a test surface and adding an antigen complex to the mixture of urine and anti-serum, said antigen complex consisting of solid particles coated with the antigen, the improvement which comprises performing the test on a test surface having a concave curvature sufficient to produce a discernible pattern where agglutination occurs, the absence of said pattern being an indication of the inhibition of agglutination by soluble antigens present in the body fluid, said test surface being a portion of a sphere having a depth of from about 3.08 mm. to about 7.30 mm. and a diameter between about 40 mm. and 65 mm.

8. The method of claim 7 wherein the curved test surface is a glass surface.

9. The method of claim 7 wherein the curved test surface is a plastic surface.

10. The method of claim 7 wherein the solid particles are polystyrene particles.

11. The method of claim 10 wherein the anti-serum additionally contains a dye.

12. The method of claim 11 wherein the dye is mint-green dye.

13. In an immunochemical test for the diagnosis of pregnancy, wherein the end point is determined by the presence or absence of agglutination, which comprises reacting a urine specimen with a complex containing antibodies to human chorionic gonadotrophin on a test surface, said complex consisting of solid particles coated with said antibodies, the improvement which comprises performing the test on a test surface having a concave curvature sufficient to produce a discernible pattern where agglutination occurs, the absence of a pattern being an indication of the absence of HCG in the urine specimen, wherein the test surface is a portion of a sphere having a depth from about 3.08 mm. to about 7.30 mm. and a diameter between about 40 mm. and 65 mm.

* * * * *

UNITED STATES PATENT AND TRADEMARK OFFICE
CERTIFICATE OF CORRECTION

PATENT NO. : 3,955,923
DATED : May 11,1976
INVENTOR(S) : Samuel Simon Asculai

It is certified that error appears in the above—identified patent and that said Letters Patent are hereby corrected as shown below:

Under the filing date of the above-identified patent, "Jan.13,1973" should read --- Jan.31,1973 ---.

Signed and Sealed this

Twenty-ninth Day of March 1977

[SEAL]

Attest:

RUTH C. MASON
*Attesting Officer*

C. MARSHALL DANN
*Commissioner of Patents and Trademarks*